US00PP34225P2

(12) United States Plant Patent
Hansen

(10) Patent No.: US PP34,225 P2
(45) Date of Patent: May 10, 2022

(54) ***HOSTA* PLANT NAMED 'SILVER BULLET'**

(50) Latin Name: ***Hosta* hybrid (Tratt.)**
Varietal Denomination: Silver Bullet

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,989

(22) Filed: Jan. 10, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12; A01H 5/02
See application file for complete search history.

*Primary Examiner* — Keith O. Robinson

(57) ABSTRACT

A new and distinct *Hosta* plant named 'Silver Bullet' producing small-sized rounded mounds of dense, basal, cordate to nearly rounded, flat, leaves with broadly acute to rounded apices, cordate bases and slightly impressed veins. The leaves are highly-glaucous intense bluish-green and hold their color through the season. The campanulate flowers are pale lavender striped opening just above the foliage beginning in early July for about two weeks. 'Silver Bullet' is useful in the landscape, as a container plant, a specimen or en masse.

2 Drawing Sheets

Botanical classification: *Hosta* hybrid (Tratt.).
Variety denomination: 'Silver Bullet'.

STATEMENT REGARDING PRIOR DISCLOSURES UNDER 37 CFR 1.77(B)(6)

*Hosta* 'Silver Bullet' was first introduced by the inventor as a non-enabling description in registration of the name in early 2021 with the International Cultivar Registration Authority for the genus *Hosta*. No plants of *Hosta* 'Silver Bullet' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Silver Bullet' hereinafter also referred to as the new plant or by the cultivar name, 'Silver Bullet'. *Hosta* 'Silver Bullet' was hybridized by the inventor on Jul. 11, 2013 at a wholesale perennial nursery in Zeeland, Mich., USA. The female parent was the proprietary, unnamed unreleased streaked sport of 'Love Pat' (not patented) and the male parent was the proprietary, unnamed unreleased hybrid known only as H10-210-2 (not patented). The seeds from this cross were planted in the fall of 2013 and a single seedling selection from this cross eventually produced the new plant. The new plant was assigned the breeder code 13-83-1 and passed the initial evaluation in the summer of 2018. 'Silver Bullet' has been asexually propagated by division at the same nursery since 2018 and also by careful shoot tip plant tissue culture with the resultant asexually propagated plants having retained all the same traits as the original plant. *Hosta* 'Silver Bullet' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Dorset Blue' (not patented), 'Blue Boy' (not patented), 'Blue Chip' (not patented), 'Blue Ice' (not patented), 'Buckshaw Blue' (not patented), 'Hadspen Blue' (not patented), 'Love Pat' (not patented), 'Prairie Sky' U.S. Plant Pat. No. 17,309, 'Blue Elf' U.S. Plant Pat. No. 30,832, 'Blue Mouse Ears' (not patented) and 'Blue Biscuit' (not patented).

The female parent is larger in habit with larger, more cupped and bullate leaves that are less glaucous and streaked with yellow and bluish-green, and the scapes are longer with more flowers per scape. The male parent has a larger, broader and more horizontal habit, the foliage is green and the scapes, more floriferous and taller and it sets seeds more readily.

The habit of 'Dorset Blue' is smaller and slower growing with leaves that are longer than wide. 'Blue Boy' is larger in habit, the foliage is more cordate and less rounded, and leaf color is more greenish. 'Blue Chip' has a smaller habit with smaller foliage and the foliage color has a less bluish-green hue. 'Blue Ice' is slower growing, has a smaller habit and smaller foliage, the leaf color is a lighter blue and the leaf shape is more cupped and cordate. 'Buckshaw Blue' is larger in habit with foliage that is more cordate and less rounded. 'Hadspen Blue' has leaves that are more cordate, more bullate. 'Love Pat' has a larger plant with foliage that is more bullate and cupped and the scapes are longer with more flowers. 'Prairie Sky' has a larger habit with larger more bullate foliage and flowers on shorter scapes over shorter period. 'Blue Elf' has a smaller habit with smaller, with less glaucous, lighter-substance (thinner) foliage. 'Blue Mouse Ears' has a shorter habit with less glaucous and lighter-substance foliage and the flowers are darker lavender colored with purple stripes. 'Blue Biscuit' has a smaller habit with smaller, with less glaucous, more cupped, more bullate and lighter-substance foliage.

Other *Hosta* cultivars may have individual traits similar to 'Silver Bullet', but the new plant differs from the above listed cultivars and all other *Hostas* known to the applicant, by the combination of the following traits.

1. Leaves are small-sized, cordate to nearly rounded, and heavy substance with broadly acute to rounded apices and cordate bases;
2. Leaves are mostly flat with slightly impressed veins;
3. Leaf color is an intense bluish-green and holds well through the season;
4. Campanulate flowers with narrow apices are pale lavender on short bluish-green scapes just above the foliage beginning in early-July;
5. Flowers are densely arranged on scapes with the first flowers beginning to open just above the foliage;
6. The habit is a small-sized rounded mound with leaves densely packed.

BRIEF DESCRIPTION OF THE DRAWINGS

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show a seven-year-old plant of 'Silver Bullet' in a shaded trial garden at a nursery in Zeeland, Mich. with supplement fertilizer and water as needed.

DETAILED BOTANICAL DESCRIPTION

Figure 1:
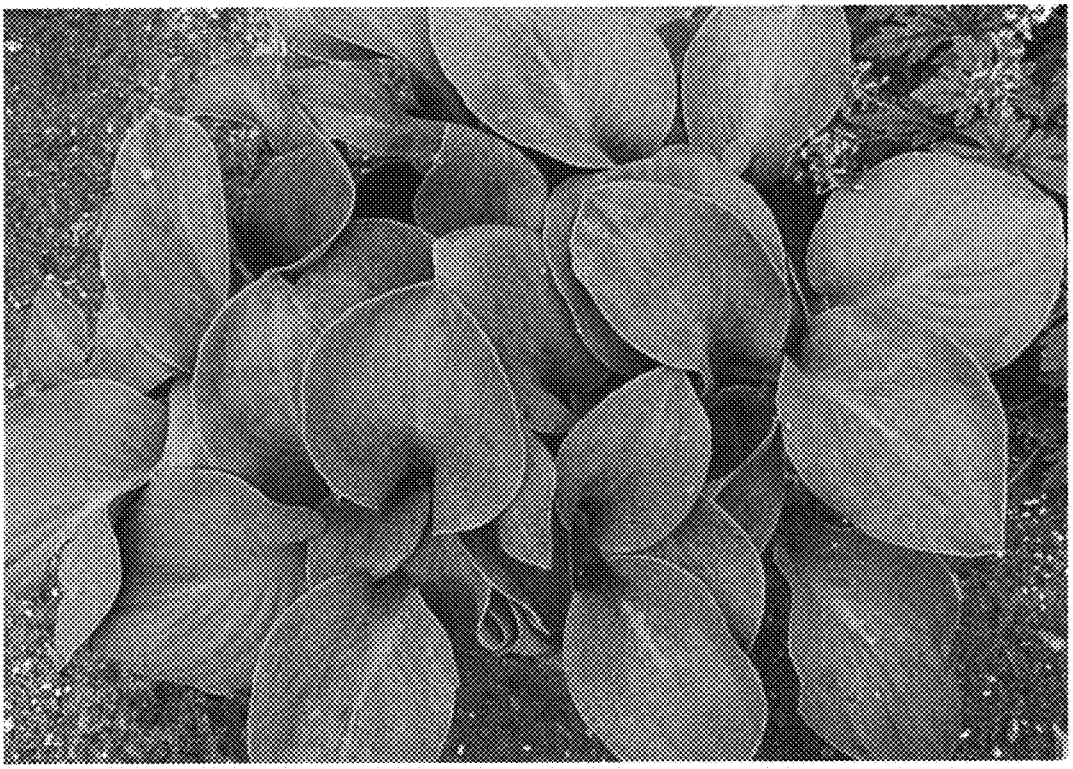
FIG. 1 shows the landscape foliage habit of a plant in late summer.
Figure 2:
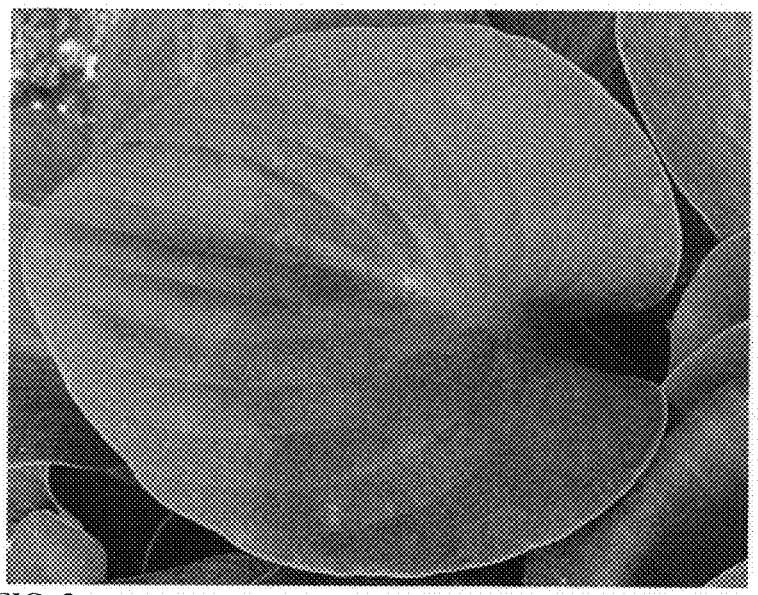
FIG. 2 shows a close-up of a leaf of a plant.
Figure 3:
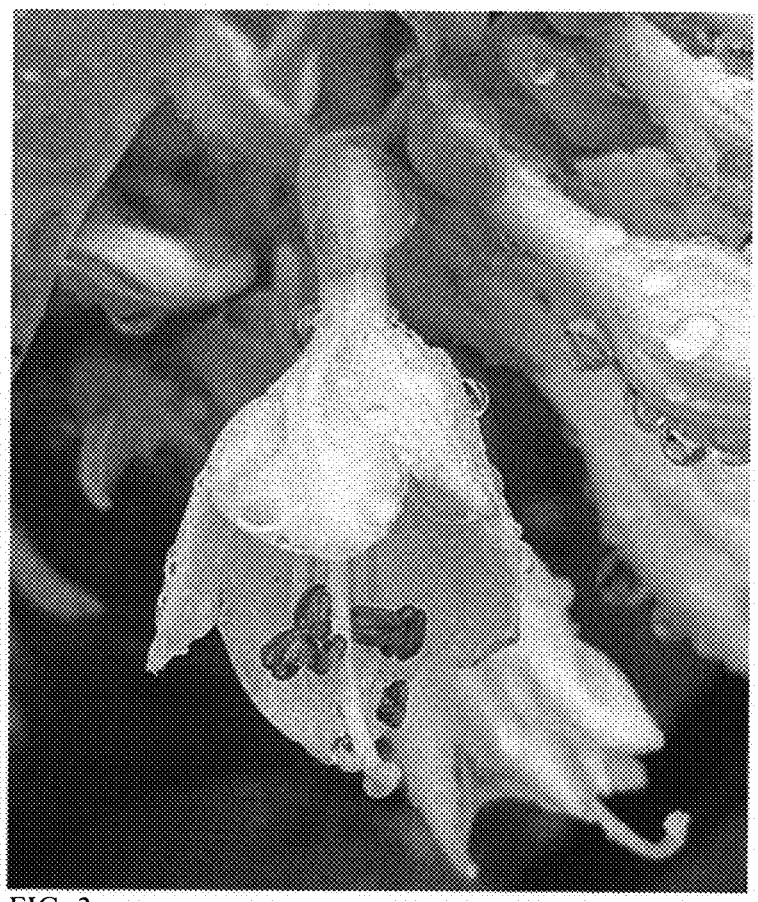
FIG. 3 shows a close-up of a flower and bud.

The following descriptions and color references are based on the 2015 edition of The Royal Horticultural Society Colour Chart except where common dictionary terms are used. The new plant, *Hosta* 'Silver Bullet', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a seven-year-old plant in a shaded trial garden in Zeeland, Mich. with supplemental water and fertilizer.

Botanical classification: *Hosta* x hybrid;

Parentage: Female or seed parent is a proprietary streaked sport of 'Love Pat'; male or pollen parent is H10-210-2, a hybrid of 'Blue Mouse Ears';

Propagation: Garden division and sterile shoot tip tissue culture;

Time to initiate roots from tissue culture: About three weeks; Docket No. HSSBU-21.53 Page 4 of 10

Growth rate: Slow;

Crop time: About five months to seven months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a medium-sized mound of outwardly to slightly upwardly petioles and leaves and mostly outwardly angled scapes flowering slightly above the foliage;

Plant size: Foliage height to about 28 cm above soil line to the top of the leaves, to about 33 cm tall to the top of the flowers and to about 56 cm wide at the widest point just above the soil line;

Foliage description: Rounded to nearly cordate; broadly acute to rounded apex, cordate base; margin entire; flat, not sinuate; not bullate; veins moderately impressed; glabrous and highly glaucous both surfaces; flexible; not variegated;

Leaf blade size: To about 12.7 cm long and about 12.7 cm wide about halfway from the apex; average about 11.2 cm long and 10.5 cm wide;

Leaf blade color: Early season and expanding adaxial between RHS N138A and RHS 137A, abaxial between RHS 146A and RHS N138A; mid-season and mature adaxial between RHS 137A and RHS N189D with wax and with wax removed between RHS 131A and RHS 139A, abaxial between RHS 138A and RHS 191D with wax, and nearest RHS 138A without wax;

Veins: 8 to 10 pairs with midrib; slightly impressed adaxial and slightly costate and smooth abaxial;

Vein color: Young adaxial nearest RHS 138A and abaxial nearest RHS 138B; mature adaxial nearest RHS 191B with proximal midrib variable, nearest RHS 115D and between RHS 145C and RHS 145D, and abaxial nearest RHS 191B;

Petiole: Glabrous and glaucous both adaxial and abaxial; moderately concavo-convex proximally and shallowly distally; stiff; outwardly; to 17 cm long, 20 mm wide at base, broadening to about 24 mm before blade, about 5 mm deep at base, average about 15 cm long and 9 mm wide and 4 mm deep;

Petiole color: Adaxial nearest RHS N138B, abaxial nearest RHS N138B with midrib nearest RHS 145B;

Flower description:

Buds one to two days prior to opening: Clavate with broadly acute apex and narrow tube and rounded base; about 32 mm long and 11 mm in diameter at the widest portion in the bulb, tube to about 14 mm long and to about 3 mm diameter at base, tapering rapidly beyond bulb;

Bud color one to two days prior to opening: Corolla tube between RHS 193B and RHS NN155D, bulb between RHS 76B and RHS 76D, less pigmented closer to opening;

Flowers: Perfect; incomplete; campanulate; attitude outwardly to slightly drooping; to 41 mm long to exserted pistil; corolla to 38 mm long and 25 mm wide at apex, fused in basal 18 mm, free in the distal 7 mm, decreasing in size distally; corolla tube portion 16 mm long and rapidly tapering to 3 mm diameter at base; with rounded base; flowers tightly arranged on scape;

Flowering lasting: Persists for a normal period, usually individually about one day on plant;

Flowering period: Scapes remain effective with flowers beginning early July for about two weeks; with about 10 to 12 flowers per scape; mostly secund;

Fragrance: No detectable fragrance;

Tepal: Two sets of three; clavate; entire margins; acute apex; fused in basal 18 mm; glabrous adaxial and abaxial; inner set to about 7 mm wide and 38 mm long; outer set to about 6 mm wide and 38 mm long;

Tepal color: Outer set adaxial distally between RHS NN155D and RHS 76D in 3 mm longitudinal center and nearest RHS NN155C along edges, abaxial nearest RHS 76D; inner set between RHS NN155D and RHS 76D in 3 mm longitudinal center and nearest RHS NN155C along edges, abaxial between RHS NN155D and lighter than RHS 76D, with a 0.5 mm translucent margin; corolla tube adaxial nearest RHS NN155C, abaxial between RHS NN155D and RHS 93B;

Gynoecium: Single; to about 41 mm long; superior;

*Style*.—Cylindrical; glabrous; to about 36 mm long and 0.7 mm diameter; straight with distal 5 mm arcuate upwards to about 90°; color nearest RHS 157C.

*Stigma*.—Puberulent; tri-lobed; about 1 mm long and 1 mm diameter; color between RHS 157D and RHS 157C.

*Ovary*.—Ellipsoidal; superior; apex rounded; base rounded to truncate; sides smooth, about 4 mm long and 2.5 mm diameter; color nearest RHS 145A.

Androecium: Six;

*Filaments*.—Six; cylindrical; approximately 38 mm long and 0.5 mm in diameter; curved or bent upwardly about 90° in the distal 5 mm; color in distal one-half nearest RHS NN155B transitioning to nearest RHS 145D in the proximal one-third.

*Anthers*.—Oblong with rounded apices; basifixed, longitudinally dehiscent; about 3.5 mm long and 2 mm wide when fully developed; color between RHS 166C and RHS 166B.

*Pollen*.—Abundant; spherical; less than 0.1 mm long; color nearest RHS 21B.

Peduncle: Cylindrical; usually one per mature division; about four per plant; glabrous; moderately glaucous; angular to arching; to about 33 cm long, and about 6 mm in diameter at base, average about 29 cm tall and 5 mm diameter at base;

Inflorescence: Flowering portion to about 6 cm long and 5 cm wide; with single bract subtending each flower; about 110 to 12 flowers per inflorescence;

Peduncle color: Between RHS N138C and RHS 138A;

Pedicel: Cylindrical; glabrous; slightly glaucous; to about 7 mm long and 2 mm diameter, decreasing distally; attitude outwardly in flower;

Pedicel color: Nearest RHS 193A;

Floral bracts: Each flower normally subtended by a single bract; ovate; acute apex and truncate base; entire margin; glabrous and slightly glaucous abaxial and adaxial; to about 10 mm long 5 mm wide, decreasing distally;

Bract color: Between RHS N138C and RHS 138A;

Fruit: Not yet observed, but fecundity unknown;

Seeds: Not yet observed;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The new plant grows best and shows best coloration with plenty of moisture, adequate drainage and light shade, but is able to tolerate some drought when mature.

Hardiness: at least from USDA zone 3 through 8, and other disease resistance is typical of that of other *Hostas*.

It is claimed:

1. A new and distinct *Hosta* plant named *Hosta* 'Silver Bullet' as herein described and illustrated.

* * * * *